US00PP27412P2

(12) United States Plant Patent
Probst

(10) Patent No.: US PP27,412 P2
(45) Date of Patent: Nov. 22, 2016

(54) ***COREOPSIS* PLANT NAMED 'RAZZLE DAZZLE'**

(50) Latin Name: ***Coreopsis* hybrid**
Varietal Denomination: Razzle Dazzle

(71) Applicant: Darrell R. Probst, Hubbardston, MA (US)

(72) Inventor: Darrell R. Probst, Hubbardston, MA (US)

( * ) Notice: Subject to any disclaimer, the term of this patent is extended or adjusted under 35 U.S.C. 154(b) by 3 days.

(21) Appl. No.: 14/545,431

(22) Filed: May 4, 2015

(51) Int. Cl.
*A01H 5/02* (2006.01)

(52) U.S. Cl.
USPC ..... Plt./417

(58) Field of Classification Search
USPC ..... Plt./417
See application file for complete search history.

*Primary Examiner* — Annette Para
(74) *Attorney, Agent, or Firm* — Penny J. Aguirre

(57) ABSTRACT

A new cultivar of hybrid *Coreopsis* plant named, 'Razzle Dazzle', that is characterized by its densely branched, compact, sturdy plant habit, its small, nearly sterile inflorescences with ray florets that are white in color with a large bright purple eye, its floriferous and long bloom season that does not require deadheading, its cold hardiness at least to U.S.D.A. Zone 5, and its resistance to powdery mildew and leaf spot.

2 Drawing Sheets

Botanical classification: *Coreopsis* hybrid.
Variety denomination: 'Razzle Dazzle'.

BACKGROUND OF THE INVENTION

The present invention relates to a new and distinct cultivar of a plant botanically of hybrid origin and known as *Coreopsis*. The new cultivar will be referred to hereafter by its cultivar name 'Razzle Dazzle'. 'Razzle Dazzle' is an herbaceous perennial grown for landscape and container use.

The new invention arose from an ongoing controlled breeding program in Hubbardston, Mass. The objective of the breeding program is to develop hybrid cultivars of *Coreopsis* with unique and superior garden attributes. In particular, to develop long-lived cultivars, in a wide range of flower colors and plant forms, that are sturdy, exhibit a true perennial habit, and are cold hardy to at least U.S.D.A Zone 5.

The new cultivar arose from a cross made by the Inventor in August of 2010 in his test garden in Hubbardston, Mass. between an unnamed, proprietary plant in the Inventor's breeding program, reference no. J 06-1 (not patented), as the female parent and pollen that was pooled from a variety of unnamed, proprietary plants (not patented) from his breeding program as the male parent (all nearly sterile). The exact male parentage is therefore unknown. 'Razzle Dazzle' was selected in September of 2011 as a single unique plant amongst the resulting seedlings.

Asexual reproduction of the new cultivar was first accomplished by stem cuttings under the direction of the Inventor in Kensington, Conn. in September of 2011. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Razzle Dazzle' as unique cultivar of *Coreopsis*.

1. 'Razzle Dazzle' exhibits a densely branched, compact, sturdy plant habit reaching an average of 40 cm in height and 50 cm in width.
2. 'Razzle Dazzle' exhibits small, nearly sterile inflorescences with ray florets that are white in color with a large bright purple eye.
3. 'Razzle Dazzle' exhibits a floriferous and long bloom season that does not require deadheading, beginning in early July and lasting until hard frost in Kensington, Conn.
4. 'Razzle Dazzle' exhibits cold hardiness at least to U.S.D.A. Zone 5.
5. 'Razzle Dazzle' exhibits resistance to powdery mildew and leaf spot.

The female parent of 'Razzle Dazzle', J 06-1, differs from 'Razzle Dazzle' in having flowers that are bright yellow in color, in being taller in height, and in having stems that tend to flop. 'Razzle Dazzle' can be compared to the *Coreopsis* cultivars 'Show Stopper' (U.S. Plant Pat. No. 22,671) and 'Snowberry' (U.S. Plant Pat. No. 18,560). 'Show Stopper' is similar to 'Razzle Dazzle' in having flowers that are primarily purple in color. 'Show Stopper' differs from 'Razzle Dazzle' in being much taller in height and in having a more open plant habit. 'Snowberry' is similar to 'Razzle Dazzle' in having a compact plant habit and in having inflorescences with ray florets that are white and purple. 'Snowberry' differs from 'Razzle Dazzle' in having flowers that are primarily white in color with a small purple eye and in being susceptible to powdery mildew when grown under similar conditions.

BRIEF DESCRIPTION OF THE DRAWINGS

The accompanying colored photographs illustrate the overall appearance and distinct characteristics of the new *Coreopsis*. The photographs were taken of a three month-old plant of 'Razzle Dazzle' as grown outdoors in a one-gallon container from a 30-cell liner in Kensington, Conn.

The photograph in FIG. 1 provides a top view of a plant of 'Razzle Dazzle' in bloom.

Figure 1:
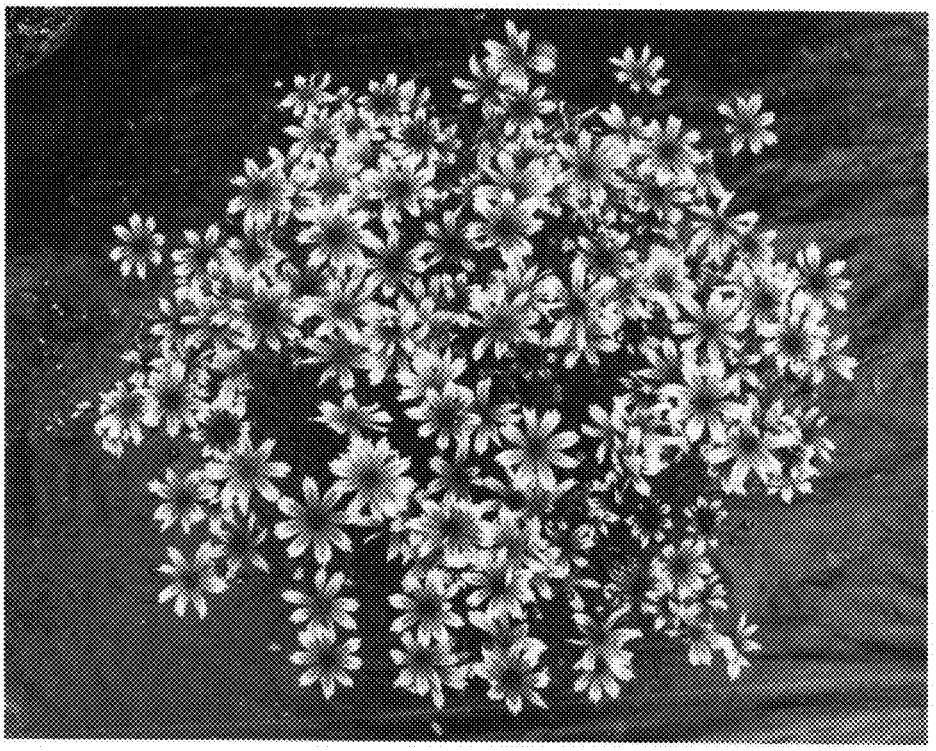
Figure 2:
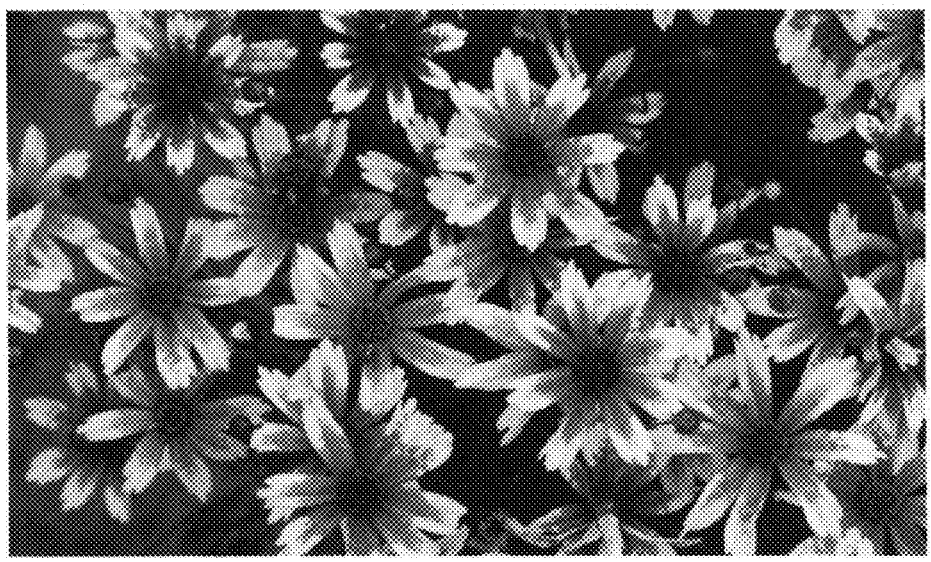

The photograph in FIG. 2 provides a close-up view of the inflorescences of 'Razzle Dazzle'.

The colors in the photographs are as close as possible with the digital photography techniques available, the color values cited in the detailed botanical description accurately describe the colors of the new *Coreopsis*.

DETAILED BOTANICAL DESCRIPTION

The following is a detailed description of three month-old plants of 'Razzle Dazzle' as grown outdoors in a one-gallon container from 30-cell liners in Kensington, Conn. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color, terms of ordinary dictionary significance are used.

General description:

*Blooming period*.—Blooms from early July until hard frost in Connecticut.

*Plant type*.—Herbaceous perennial.

*Plant habit*.—Clump-forming, densely branched, compact.

*Height and spread*.—An average of 40 cm in height and 50 cm in width.

*Cold hardiness*.—At least in U.S.D.A Zone 5.

*Diseases resistance*.—Has been observed to be highly resistant to powdery mildew (*Podosphaera macularis*) and leaf spot (*Pseudomonas cichorii*).

*Root description*.—Fibrous when young, becoming fleshy with age.

*Propagation*.—Stem cuttings.

*Growth rate*.—Moderate.

Stem description:

*Shape*.—Oval, ridged.

*Stem color*.—Young; 144A to 144B, mature; 141A.

*Stem size*.—Main and secondary stems; an average of 27 cm in length and 1.5 mm in width, tertiary stems; 8.5 cm in length and 1 mm in width.

*Stem surface*.—Glabrous.

*Stem aspect*.—Upright.

*Branching habit*.—Well-branched, an average of 5 main branches, 3 secondary branches per main stem, and 3 tertiary branches.

*Internode length*.—An average of 3 cm.

Foliage description:

*Leaf division*.—Simple.

*Leaf margins*.—Entire to trifid.

*Leaf size*.—Variable, up to 5.5 cm in length and 4 mm in width when entire, up to 4.5 cm in length and 2 cm in width when lobed.

*Leaf shape*.—Oblanceolate to ensiform when entire, lobes oblanceolate to ensiform.

*Leaf base*.—Truncate.

*Leaf apex*.—Acute.

*Leaf venation*.—Pinnate, inconspicuous, matches leaf color on upper and lower surface.

*Leaf attachment*.—Sessile.

*Leaf arrangement*.—Opposite.

*Leaf surface*.—Glabrous on upper and lower surface.

*Leaf color*.—Young upper and lower surface; 143A to 143B, mature upper and lower surface; 137A.

Inflorescence description:

*Inflorescence type*.—Composite with a single row of ray florets surrounding disk florets in the center, forming a radiant head, inflorescences are borne on branch terminals in loose corymbs.

*Lastingness of inflorescence*.—8 to 10 days until senescence of ray flowers, longer in cool temperatures, bracts and disk flowers are persistent.

*Fragrance*.—None detected.

*Quantity of inflorescences*.—An average of 30 per main branch.

*Inflorescence size*.—Corymbs; an average of 6 cm in length and width, composite; an average of 1 cm in depth and up to 4 cm in diameter.

*Inflorescence buds*.—An average of 4 mm in depth and in diameter, spherical in shape with a flattened top, color; a blend of 137C and 163A to 163B with N186A at the top center.

*Peduncle*.—An average of 3.5 cm in length and 1 mm in width, glabrous surface, 144A to 144B in color.

*Pedicle*.—An average of 3 cm in length and 0.8 mm in width, glabrous surface, 144A to 144B in color.

*Sepals*.—An average of 7, 3 mm in length and 1 mm in width, color; a blend of 144A and 137C with margins 150C.

Involucral bracts:

*Bract number*.—8 total, 4 outer bracts and 4 inner bracts.

*Bract arrangement*.—Bracts are un-fused and overlapping surrounding the receptacle in a campanulate form and held close to lower surface of ray florets.

*Bract size*.—Outer and inner bracts; an average of 1.2 cm in length and 2.5 mm in width.

*Bract color*.—Inner bracts and outer bracts translucent; apex, 13A, base 137C, and margins 2C.

*Bract texture*.—Glabrous on outer and inner surfaces of outer and inner bracts.

*Bract apex*.—Acute to rounded on outer and inner bracts.

*Bract base*.—Truncate on inner and outer bracts.

*Bract margins*.—Entire on outer and inner bracts.

*Bract shape*.—Outer and inner bracts; oblanceolate to oblong.

Ray florets (sterile):

*Number*.—An average of 8 arranged primarily in one row.

*Shape*.—Oval to oblong.

*Size*.—An average of 1.7 cm in length and 6 mm in width.

*Apex*.—2 notched.

*Base*.—Cuneate.

*Margins*.—Entire with apex notched.

*Aspect*.—Held outward to slightly upward.

*Texture*.—Glabrous on upper and lower surface.

*Color*.—When opening and when fully open upper surface; 2A to 2D with base (large eye) N186D, when opening and when fully opened lower surface; 2D with base (large eye) a blend of 64A and 59B.

Disk flowers (perfect):

*Shape*.—Tubular, corolla is fused, flared at apex.

*Number*.—About 80.

*Size*.—About 4 mm in length and 0.7 mm in width.

*Color*.—En masse; 183A, corolla tube 2A to 2C; with apices 178A to 178D in color.

*Receptacle*.—About 3 mm in diameter and 1 mm in depth, a 139B in color.

Reproductive organs:

*Presence*.—Disk flowers are perfect, ray flowers are sterile.

*Gynoecium*.—1 Pistil, 4 mm in length, style is very fine, translucent and 2D in color, stigma is 178A in color, ovary is 1 mm in length, 0.5 mm in width, inferior, and 2C in color.

*Androcoecium*.—5 stamens, fused into tube surrounding style, 2 mm in length and 0.2 mm in width, about N186C in color, pollen is very low in quantity.

*Fruit/seed*.—No fruit or seed development was observed.

It is claimed:

1. A new and distinct cultivar of *Coreopsis* plant named 'Razzle Dazzle' as herein illustrated and described.

* * * * *